(12) United States Patent
Tsunomori et al.

(10) Patent No.: US 11,896,418 B2
(45) Date of Patent: Feb. 13, 2024

(54) RECORDING MEDIUM, MOVING IMAGE MANAGEMENT APPARATUS, AND MOVING IMAGE DISPLAY SYSTEM

(71) Applicant: Konica Minolta, Inc., Tokyo (JP)

(72) Inventors: Akinori Tsunomori, Kodaira (JP); Taketoh Muraoka, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 331 days.

(21) Appl. No.: 17/314,399

(22) Filed: May 7, 2021

(65) Prior Publication Data

US 2021/0345981 A1 Nov. 11, 2021

(30) Foreign Application Priority Data

May 11, 2020 (JP) .................................. 2020-082951

(51) Int. Cl.
*A61B 6/00* (2006.01)
*G06T 7/00* (2017.01)
*G06T 7/20* (2017.01)

(52) U.S. Cl.
CPC ............ *A61B 6/5288* (2013.01); *A61B 6/463* (2013.01); *A61B 6/5217* (2013.01); *A61B 6/5294* (2013.01); *A61B 6/54* (2013.01); *G06T 7/0016* (2013.01); *G06T 7/20* (2013.01); *G06T 2207/10016* (2013.01); *G06T 2207/10124* (2013.01); *G06T 2207/30061* (2013.01)

(58) Field of Classification Search
None
See application file for complete search history.

(56) References Cited

U.S. PATENT DOCUMENTS

2017/0095197 A1* 4/2017 Kleiner .................. A61B 6/486

FOREIGN PATENT DOCUMENTS

| JP | 2004000412 A | 1/2004 |
|---|---|---|
| JP | 2017-176828 A | 10/2017 |
| JP | 2019092612 A | 6/2019 |
| JP | 2019-187862 A | 10/2019 |

OTHER PUBLICATIONS

Office Action issued for the related Japanese Application No. 2020-082951, dated Aug. 29, 2023, along with its English translation, 7 pages.
Office Action dated Nov. 7, 2023, for the corresponding Japanese Application No. 2020-082951, with English translation.

* cited by examiner

*Primary Examiner* — Hoon K Song
(74) *Attorney, Agent, or Firm* — LUCAS & MERCANTI, LLP (57) ABSTRACT

A non-transitory recording medium storing a computer readable program that causes a computer of a moving image management apparatus, which manages a radiographic moving image, to perform: obtaining that is obtaining a first radiographic moving image and a second radiographic moving image, the first radiographic moving image showing a movement of a subject while breathing is repeated a first number of times per unit time, and the second radiographic moving image showing a movement of the subject while breathing is repeated a second number of times that is different from the first number of times per the unit time; and associating that is associating respective numbers of breaths during imagings with the first radiographic moving image and the second radiographic moving image that are obtained in the obtaining.

12 Claims, 4 Drawing Sheets

RECORDING MEDIUM, MOVING IMAGE MANAGEMENT APPARATUS, AND MOVING IMAGE DISPLAY SYSTEM

CROSS-REFERENCE TO RELATED APPLICATIONS

The entire disclosure of Japanese Patent Application No. 2020-082951 filed on May 11, 2020 is incorporated herein by reference in its entirety.

BACKGROUND

Technological Field

The present invention relates to a recording medium, a moving image management apparatus, and a moving image display system.

Description of the Related Art

There is so called Chronic Obstructive Pulmonary Disease (hereinafter, referred to as COPD) as one of pulmonary diseases.

The COPD is a disease of airway or alveolar damaged by the cigarette smoke and the like. The patient affected with the COPD may have a symptom called pulmonary hyperinflation that the lungs inflate since full exhalation cannot be performed.

Various types of techniques have been conventionally suggested in order to check the state of such pulmonary hyperinflation.

For example, JP 2017-176828 A describes a respiratory function testing apparatus including a setting unit that can set a reference period and a guide notification unit that executes guide notification for guiding the breathing period of a subject to the reference period which was set.

JP 2019-187862 A describes a radiographic image analysis apparatus including a lung field area calculation unit that calculates the area of a lung field from a chest image obtained by radiation imaging of the chest in one direction, and an estimation unit that estimates a residual air volume, a functional residual capacity, a total lung capacity or a residual volume ratio of the lung field, based on the calculated lung field area.

SUMMARY

The pulmonary hyperinflation which is caused in accordance with the breathing on exertion (for example, when the patient is walking or running) is particularly called dynamic pulmonary hyperinflation. Whether the dynamic pulmonary hyperinflation occurs in the patient or not depends on the degree of exertion performed by the patient. That is, the dynamic pulmonary hyperinflation may not occur on a light exertion (movement which can be performed with slow breathing) and may occur for the first time on a relatively heavy exertion (movement making the breathing fast). Thus, it is important for diagnosing the patient by the doctor to grasp the degree of exertion at which the dynamic pulmonary hyperinflation occurs in the patient.

It is also important for knowing the degree of recovery of the patient to grasp the change of manner in which the dynamic pulmonary hyperinflation occurs after receiving the treatment.

Thus, there is required a method which can easily and accurately obtain multiple pieces of respiratory data for different numbers of breaths (respirations) per unit time and multiple pieces of respiratory data for the same number of respirations which were obtained on different obtaining dates.

However, the respiratory function testing apparatus described in JP 2017-176828 A requires the patient to perform forced expiration in addition to repeating of respiration, in order to output respiration data for diagnosis. This forced expiration is a large burden on the patient, and furthermore, makes it difficult for the patient to reproduce the same respiration as the previous respiration when the test is repeated at a same condition. When there are variations in respects other than the number of respirations between the pieces of respiration data, the doctor possibly diagnoses erroneously.

On the other hand, the radiographic image analysis apparatus described in JP 2019-187862 A generates the respiratory data on the basis of the radiographic moving image, not on the basis of the amount of exhaled breath. Thus, it is relatively easily to ensure the reproducibility of each test. However, in the diagnosis using the radiographic moving image generated by the radiographic image analysis apparatus described in JP 2019-187862 A, it has been difficult for the doctor to find out the radiographic moving images of a same imaging date and different numbers of respirations per unit time and radiographic moving images of the same number of respirations and different obtaining dates from multiple radiographic moving images.

An object of the present invention is to enable the user to easily find out radiographic moving images of a same imaging date and different numbers of respirations per unit time and radiographic moving images of a same number of respirations and different obtaining dates from among multiple radiographic moving images.

To achieve at least one of the abovementioned objects, according to an aspect of the present invention, a recording medium reflecting one aspect of the present invention is a non-transitory recording medium storing a computer readable program that causes a computer of a moving image management apparatus, which manages a radiographic moving image, to perform: obtaining that is obtaining a first radiographic moving image and a second radiographic moving image, the first radiographic moving image showing a movement of a subject while breathing is repeated a first number of times per unit time, and the second radiographic moving image showing a movement of the subject while breathing is repeated a second number of times that is different from the first number of times per the unit time; and associating that is associating respective numbers of breaths during imagings with the first radiographic moving image and the second radiographic moving image that are obtained in the obtaining.

To achieve at least one of the abovementioned objects, according to another aspect of the present invention, a moving image management apparatus reflecting one aspect of the present invention comprises a hardware processor that obtains a first radiographic moving image and a second radiographic moving image, the first radiographic moving image showing a movement of a subject while breathing is repeated a first number of times per unit time, and the second radiographic moving image showing a movement of the subject while breathing is repeated a second number of times that is different from the first number of times per the unit time, and associates respective numbers of breaths during imagings with the first radiographic moving image and the second radiographic moving image that are obtained.

To achieve at least one of the abovementioned objects, according to another aspect of the present invention, a moving image display system reflecting one aspect of the present invention comprises: a moving image generator that generates a first radiographic moving image and a second radiographic moving image, the first radiographic moving image showing a movement of a subject while breathing is repeated a first number of times per unit time, and the second radiographic moving image showing a movement of the subject while breathing is repeated a second number of times that is different from the first number of times per the unit time; and a hardware processor that associates respective numbers of breaths during imagings with the first radiographic moving image and the second radiographic moving image that are generated by the moving image generator.

BRIEF DESCRIPTION OF THE DRAWINGS

The advantages and features provided by one or more embodiments of the invention will become more fully understood from the detailed description given hereinafter and the appended drawings which are given by way of illustration only, and thus are not intended as a definition of the limits of the present invention, and wherein.

DETAILED DESCRIPTION OF EMBODIMENTS

Hereinafter, one or more embodiments of the present invention will be described with reference to the drawings. However, the scope of the invention is not limited to the disclosed embodiments or the illustrated examples.

[1. Configuration of Moving Image Display System]

First, a configuration of a moving image display system (hereinafter, system 100) according to the present embodiment will be described.

Figure 1:
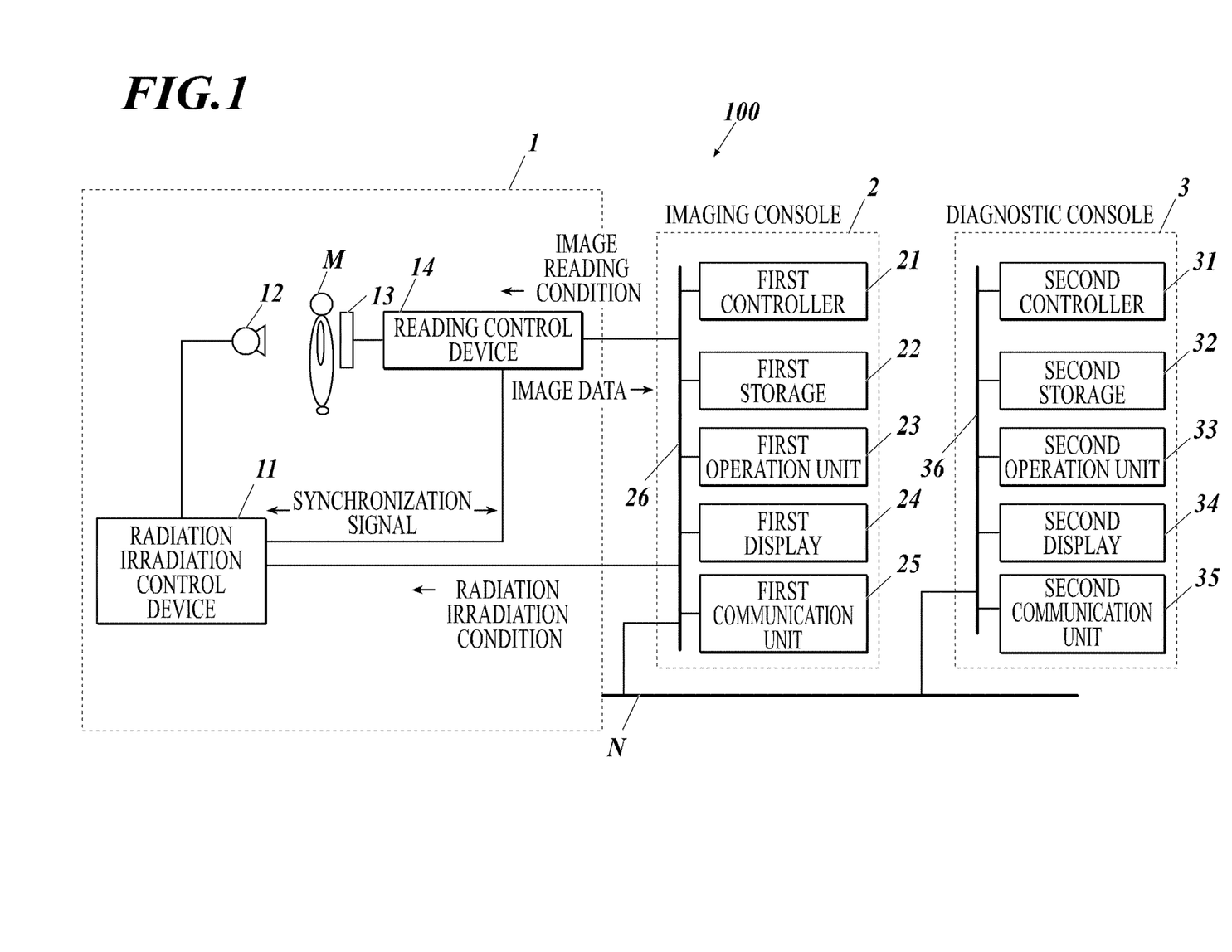
FIG. 1 is a block diagram showing a moving image display system according to an embodiment of the present invention.

FIG. 1 is a block diagram showing the system 100.

As shown in FIG. 1, the system 100 includes an imaging apparatus 1, an imaging console 2, and a diagnostic console 3.

These components can communicate with each other via a communication network N.

The apparatuses forming the system 100 are based on the DICOM (Digital Image and Communications in Medicine) standard, and the communication between the apparatuses are performed according to the DICOM standard.

The system 100 may be connected to a hospital information system (HIS), a radiology information system (RIS), an image analysis device, a picture archiving and communication systems (hereinafter, referred to as PACS) and the like not shown in the drawings.

(1-1. Imaging Apparatus)

The imaging apparatus 1 is capable of moving image imaging (imaging to obtain a moving image) of the movement of the imaging target site of a subject M (for example, movement having a cycle such as a state change of inflation and deflation in lungs, a heartbeat and the like caused by the respiratory movement.).

The imaging apparatus 1 includes a radiation irradiation control device 11, a radiation source 12, a radiation detector 13, and a reading control device 14.

The radiation irradiation control device 11 controls the radiation source 12 on the basis of radiation irradiation conditions which were input from the imaging console 2.

The radiation irradiation conditions include, for example, a pulse rate, a pulse width, a pulse interval, the number of imaging frames per imaging, a value of tube current, a value of tube voltage, the type of additional filter, and an SID (shortest distance between the tube bulb of the radiation source 12 and the radiation detector 13).

The pulse rate is the number of radiation irradiations per second, and matches an after-mentioned frame rate. The pulse width is a radiation irradiation time per radiation irradiation. The pulse interval is a time from start of one radiation irradiation to start of next radiation irradiation, and matches an after-mentioned frame interval.

The radiation source 12 emits radiation (for example, X-ray) to the subject M in accordance with control of the radiation irradiation control device 11.

To be specific, the radiation source 12 repeatedly emits pulsed radiation of a predetermined irradiation time per irradiation at a set pulse rate (pulse irradiation), or continues to emit radiation of a dose lower than that of the pulsed radiation for a predetermined time.

The radiation detector 13 is arranged to face the radiation source 12 through the subject M.

The radiation detector 13 is configured by including a semiconductor image sensor such as an FPD (Flat Panel Detector). The radiation detector 13 includes a substrate not shown in the drawings, semiconductor elements that are arranged in a matrix on the substrate surface and generate electric charges corresponding to the received intensities of electromagnetic waves, and switching elements (for example, TFT (Thin Film Transistor)) that are arranged between the respective semiconductor elements and the reading control device 14.

The radiation detector 13 may be an indirect type that converts radiation into visible light with a scintillator and further converts the converted visible light into electric signals, or may be a direct type that directly converts radiation into electric signals.

The reading control device 14 controls the radiation detector 13 to obtain the image data of radiographic moving image on the basis of image reading conditions input from the imaging console 2.

The image reading conditions include a frame rate, a frame interval, a sampling pitch (pixel size), and an image size (matrix size), for example.

The frame rate is the number of frames obtained per second, and matches the pulse rate.

The frame interval is the time from start of operation obtaining one frame to the start of operation obtaining the next frame, and matches the pulse interval.

The reading control device 14 is connected to the radiation irradiation control device 11, and synchronizes the radiation irradiation operation with the image reading operation by transmitting and receiving synchronization signals to and from the radiation irradiation control device 11.

The reading control device 14 reads out the amounts of electric charges which were released by the respective semiconductor elements of the radiation detector 13 as signal values and generates one of the frames forming the moving image on the basis of the multiple signal values which were read out.

The reading control device 14 generates a radiographic moving image by repeating this frame generation a predetermined number of times.

The reading control device 14 and the radiation detector 13 form a moving image generator by performing the above-mentioned operation.

(1-2. Imaging Console)

The imaging console 2 controls the imaging apparatus 1.

The imaging console 2 according to the present embodiment also serves as a moving image management apparatus that manages the radiographic moving image. The moving image management apparatus may be provided separate from the imaging console 2.

As shown in FIG. 1, the imaging console 2 includes a first controller 21 (hardware processor), a first storage 22, a first operation unit 23, a first display 24, and a first communication unit 25.

The units 21 to 25 are electrically connected via a bus or the like.

The first controller 21 is configured by including a CPU (Central Processing Unit), a RAM (Random Access Memory) and the like.

The CPU of the first controller 21 reads out various programs stored in the first storage 22 to load them into the RAM, executes various types of processing in accordance with the loaded programs, and performs centralized control of the operations of the units in the imaging console 2.

The first storage 22 is configured by including a nonvolatile semiconductor memory, a hard disk or the like.

The first storage 22 stores programs for the first controller 21 to perform various types of processing (after-mentioned receiving processing, imaging controlling processing, moving image management processing, and the like), parameters necessary for performing the processing, and the like.

The first operation unit 23 is configured to enable the user to operate by a keyboard including cursor keys, numeric input keys and various types of function keys, a pointing device such as a mouse, a touch panel layered on the surface of the first display 24, and the like.

The first operation unit 23 outputs a control signal corresponding to the operation made by the user to the first controller 21.

The first display 24 is configured by including an LCD (Liquid Crystal Display), an ELD (Electronic Luminescent Display) and a CRT (Cathode Ray Tube), for example.

The first display 24 displays various images and the like corresponding to the display signals input from the first controller 21.

The first communication unit 25 is configured by including a communication module (LAN adapter, modem, TA (Terminal Adapter)).

The first communication unit 25 transmits and receives various signals and various types of data to and from other apparatuses (imaging apparatus 1, diagnostic console 3, and the like) which are connected via the communication network N (LAN (Local Area Network), WAN (Wide Area Network), internet, and the like).

(1-3. Diagnostic Console)

The diagnostic console 3 is a moving image analysis apparatus for supporting diagnosis by the doctor by obtaining a moving image from the imaging console 2 and displaying the obtained moving image and the analysis results of the moving image.

As shown in FIG. 1, the diagnostic console 3 includes a second controller 31 (hardware processor), a second storage 32, a second operation unit 33, a second display 34, and a second communication unit 35.

The units 31 to 35 are electrically connected via a bus or the like.

The second controller 31 is configured similarly to the first controller 21.

The second storage 32 is configured by including a nonvolatile semiconductor memory, a hard disk or the like similarly to the first storage 22. However, the stored contents are different from those of the first storage 22.

The second storage 32 stores programs for the second controller 31 to perform various types of processing (after-mentioned analysis processing, display processing, and the like), parameters necessary for performing the processing, and the like.

The second storage 32 can store image data of a radiographic moving image.

The image data in the DICOM file format includes an image portion and a header portion.

Actual data of the medical image is written to the image portion.

Various types of tag information (supplementary information) are written to the header portion.

The tag information according to the present embodiment includes patient information, test information, series information, image information, GSPS (Grayscale Softcopy Presentation State) information and the like.

The patient information includes a patient ID, a patient name, a birth date, an age, a sex, a height, and a weight, for example.

The test information includes, a test ID, a test date, a test time, the number of series, and the number of images, for example.

The series information includes, a modality, an imaging site, an imaging direction, a series number, and the number of images, for example.

The image information includes, an image number, a patient direction, a vertical width, a horizontal width, a tube voltage, mA, a tube current, a pixel interval, a frame number, and the number of frames, for example.

The second storage 32 may be divided into a storage which stores programs and the like and a storage which stores image data.

The image data may be stored in a storage device (for example, PACS) separate from the diagnostic console 3.

The second operation unit 33 is configured similarly to the first operation unit 23.

The imaging console 2 and the diagnostic console 3 may have a common operation unit. In such a case, the first operation unit 23 or the second operation unit 33 is not necessary.

The second display 34 forms a display, and is configured similarly to the first display 24.

The imaging console 2 and the diagnostic console 3 may have a common display. In such a case, the first display 24 or the second display 34 is not necessary.

At least one of the first display 24 and the second display 34 may be a display device provided separate from the console body.

The second communication unit 35 is configured similarly to the first communication unit 25.

The second communication unit 35 transmits and receives various signals and various types of data to and from other apparatuses (imaging apparatus 1, imaging console 2, and the like) which are connected via the communication network N.

(1-4. Operation Outline of Moving Image Display System)

The system 100 configured in such a way operates as follows.

First, when the user (technologist or the like) performs moving image imaging of a diagnosis target site of the subject M by using the imaging apparatus 1, the imaging apparatus 1 generates a radiographic moving image showing the diagnosis target site, and transmits the image data to the imaging console 2.

When the imaging console 2 receives the image data, the imaging console 2 executes moving image management processing (to be described later in detail), and transmits the image data to the diagnostic console 3 and other storage devices (PACS or the like).

The diagnostic console 3 displays a radiographic moving image based on the image data received from the imaging console 2.

[2. Specific Operation of Imaging Console]

Next, the specific operation of the imaging console 2 included in the above system 100 will be described.

Figure 2:
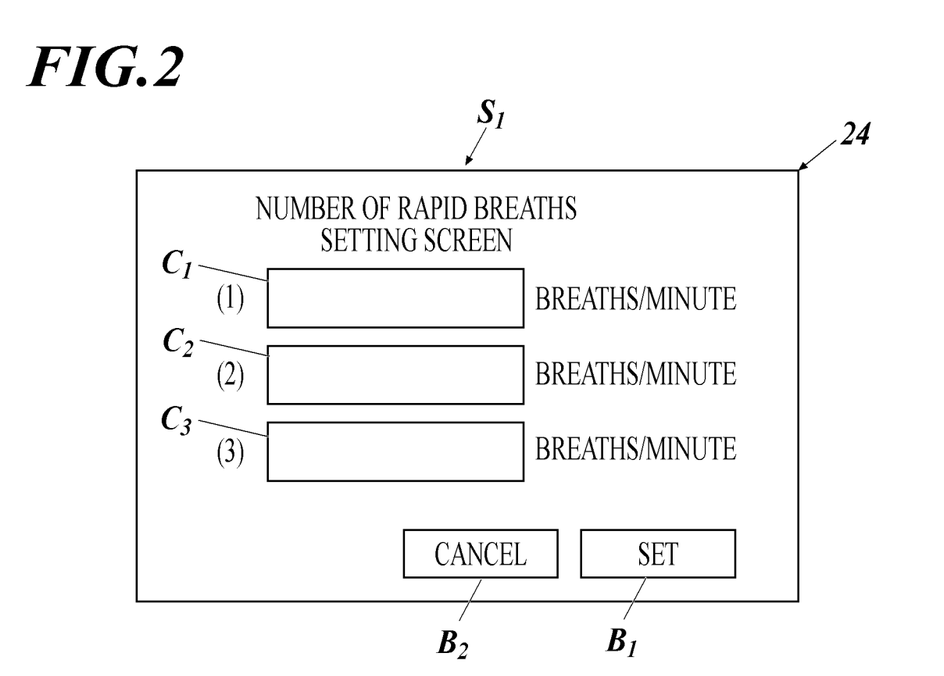
FIG. 2 is a view showing an example of a setting screen displayed by an imaging console in FIG. 1.
Figure 3:
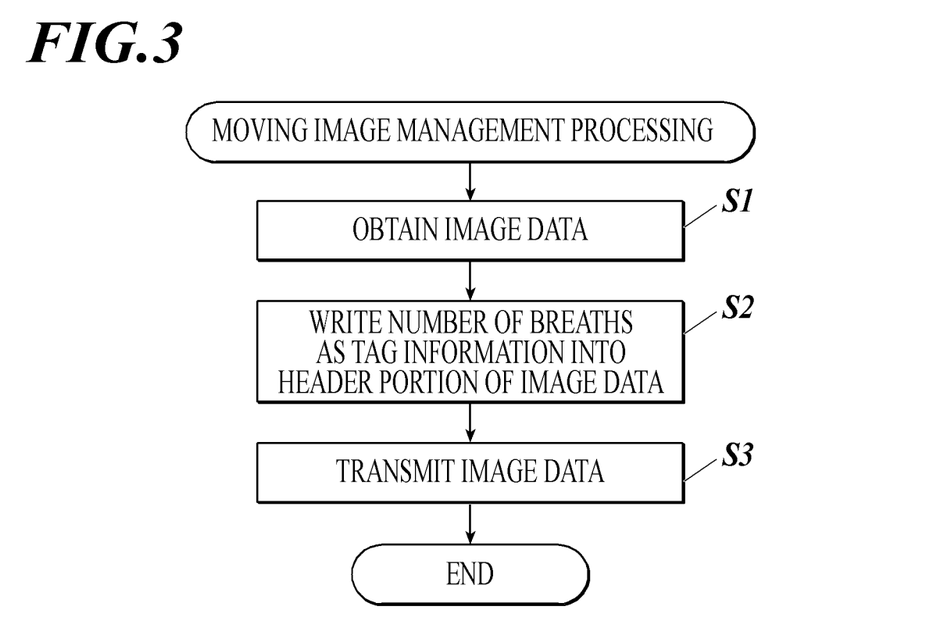
FIG. 3 is a flowchart showing the flow of moving image management processing executed by the imaging console in FIG. 1.

FIG. 2 is a view showing an example of a setting screen $S_1$ displayed by the imaging console 2, and FIG. 3 is a flow chart showing the flow of moving image management processing executed by the imaging console 2.

(2-1. Setting Operation)

The first controller 21 executes receiving processing in response to satisfaction of a predetermined condition (for example, turning on of the power of the imaging console 2, activation of application, etc.) as a trigger. In this receiving processing, the first controller 21 receives input of a first numerical value (for example, 20) and input of a second numerical value (for example, 40).

In the receiving processing according to the present embodiment, the first controller 21 also receives input of a third numerical value (for example, 60).

The first to third numerical values are numerical values to be associated with the radiographic moving images as the numbers of breaths.

In the receiving processing according to the present embodiment, the first controller 21 causes the first display 24 to display the setting screen $S_1$.

As shown in FIG. 2, the setting screen $S_1$ includes multiple numerical value input boxes $C_1$ to $C_3$, a setting button $B_1$, and a cancel button $B_2$, for example.

The first controller 21 is configured to set, as first to third numerical values, the numerical value corresponding to the operation (for example, selecting (clicking, touching or the like) any of the multiple numerical input boxes $C_1$ to $C_3$ and pressing the numerical input keys) which was performed to the first operation unit 23 when the first display 24 displays the setting screen $S_1$.

Though FIG. 2 illustrates the setting screen $S_1$ having three numerical input boxes, four or more numerical input boxes may be provided.

In the receiving processing according to the present embodiment, the first controller 21 may also receive the input of various types of imaging conditions (radiation irradiation conditions, image reading conditions, and the like).

The first controller 21 forms a receiving unit by executing such receiving processing.

(2-2. Imaging Control Operation)

The first controller 21 executes imaging controlling processing in response to satisfaction of a predetermined condition (for example, completion of imaging preparation of the radiation irradiation control device 11 and the reading control device 14, and execution of imaging instruction operation by the user) as a trigger.

In this imaging controlling processing, the first controller 21 causes the imaging apparatus 1 to perform moving image imaging.

To be specific, the first controller 21 causes the radiation irradiation control device 11 to perform the operation for the radiation source 12 to emit radiation, and causes the radiation detector 13 and the reading control device 14 to generate a radiographic moving image.

At this time, by making the subject M perform repeatedly take a breath a first number of times (for example, approximately 20 times) per unit time (for example, one minute), the radiation detector 13 and the reading control device 14 generates a radiographic moving image (hereinafter, referred to as a first radiographic moving image) showing the movement of the subject M when the subject M repeatedly took a breath the first number of times per unit time, the radiographic moving image being to be associated with the first numerical value as the number of breaths.

The first controller 21 causes the imaging apparatus 1 to end the moving image imaging in response to release of the imaging instruction operation or end of imaging for the predetermined number of frames, as a trigger.

To be specific, the first controller 21 causes the radiation irradiation control device 11 to end the operation for the radiation source 12 to emit radiation, and causes the radiation detector 13 and the reading con troll device 14 to end the generation of radiographic moving image.

(2-3. Notification Function)

The first controller 21 is configured to execute notification processing while the first controller 21 is executing the above imaging controlling processing (while the radiation detector 13 and the reading control device 14 are generating the radiographic moving image).

In this notification processing, the first controller 21 causes a notifier to repeatedly notify at least one of an expiration instruction and an inspiration instruction.

The notifier is configured by including a speaker that outputs sound, a screen that displays characters, a lamp that emits light, or the like.

The expiration instruction is instructing a subject to perform expiratory movement. The expiration instruction is, for example, saying or displaying characters "breathe out".

The inspiration instruction is instructing a subject to perform inspiratory movement. The inspiration instruction is, for example, saying or displaying characters "breathe in".

In the notification processing according to the present embodiment, the first controller 21 repeats the expiration instruction and the inspiration instruction alternately.

When the imaging controlling processing which is executed in parallel is the processing of generating the radiographic moving image to be associated with the first numerical value as the number of breaths, the first controller 21 causes the notifier to repeatedly notify the expiration instruction and the inspiration instruction the first numerical value of times per unit time.

(2-4. Moving Image Management Operation)

The first controller 21 executes moving image management processing as shown in FIG. 3 in response to satisfaction of a predetermined condition (for example, start of generation of the moving image by the imaging apparatus 1, start of transmitting the image data by the imaging apparatus 1, and execution of predetermined operation to the first operation unit 23) as a trigger.

In this moving image management processing, the first controller 21 first executes an obtaining process (step S1).

In this obtaining process, the first controller 21 obtains a first radiographic moving image from the reading control device 14.

The first controller 21 forms an obtaining unit by executing this obtaining process.

After obtaining the first radiographic moving image, the first controller 21 executes an associating process (step S2).

In this associating process, the first controller 21 associates the number of breaths when the imaging was performed with the first radiographic moving image obtained in the obtaining process.

In the associating process according to the present embodiment, the first controller 21 associates the first numerical value as the number of breaths with the first radiographic moving image.

To be specific, the first controller 21 writes the first numerical value as supplementary information of the image into the header portion of the data of the first radiographic moving image.

When it is possible to obtain the actual number of breaths of the subject by any method (for example, after-mentioned analysis operation of the diagnostic console 3), the first controller 21 may associate the actual number of breaths with the first radiographic moving image.

To be more specific, the first controller 21 writes the first numerical value into a private tag (tag having xxxx of odd number in (xxxx, yyyy)) among multiple DICOM tags in the header portion.

When the first numerical value is 20, the private tag into which the first numerical value was written is, for example, as follows:

(0031, 11F3)<SS>20

When the first numerical value is 40, the private tag into which the first numerical value was written is, for example, as follows:

(0031, 11F3)<SS>40

In the associating process according to the present embodiment, the first controller 21 also writes information such as an identification ID for identifying each radiographic moving image, subject information, test information, radiation irradiation conditions, image reading conditions, and the number indicating the imaging order (frame number), in addition to the number of breaths.

After associating of the number of breaths, the first controller 21 transmits the first radiographic moving image to the diagnostic console 3 via the first communication unit 25 (step S3), and ends the moving image management processing.

When a second numerical value (third numerical value) is input to the setting screen $S_1$, the first controller 21 according to the present embodiment repeats the operations similar to the imaging control operation, notification operation and moving image management operation which have been descried above, for the second (third) radiographic moving image.

That is, the first controller 21 executes the notification processing to make the subject M repeat breathing a second number of times different from the first number of times per unit time (third number of times different from the first number of times and the second number of times), while executing the imaging controlling processing to generate the second radiographic moving image (third radiographic moving image) showing the movement of the subject M when the subject M repeated breathing the second (third) number of times per unit time, the second radiographic moving image (third radiographic moving image) being to be associated with the second (third) numerical value in the imaging apparatus 1.

The first controller 21 executes the moving image management processing to associate the second (third) numerical value with the second (third) radiographic moving image.

Thus, it is possible to correlate the first to third radiographic moving images with each other as the radiographic moving images of a same imaging date and different numbers of breaths per unit time.

When observations are to be made over time, the first controller 21 according to the present embodiment repeats the operations similar to the imaging control operation, notification operation and moving image management operation which have been described above on a different date from the date of the generation of first (second, third) radiographic moving image on same conditions as those when the first (second, third) radiographic moving image was generated.

That is, the first controller 21 executes the notification processing to make the subject M repeat breathing the first number of times (second number of times, third number of times) per unit time, while executing the imaging controlling processing to generate the first comparative moving image (second, third comparative moving image) showing the movement of the subject M when the subject M repeated breathing the first (second, third) number of times per unit time, the first comparative moving image (second, third comparative moving image) being to be associated with the first (second, third) numerical value as the number of breaths in the imaging apparatus 1.

The first controller 21 then executes the moving image management processing to associate the first (second, third) numerical value with the first (second, third) comparative moving image.

Thus, it is possible to correlate the first to third comparative moving images with each other as the radiographic moving images of a same imaging date and different numbers of breaths per unit time, and correlate the first to third comparative moving images as the radiographic moving images of the same number of breaths as and different obtaining dates from the first to third radiographic moving images respectively.

The date on which the first to third comparative moving images are generated may be before the date on which the first radiographic moving image is to be generated or may be after the date on which the first radiographic moving image was generated.

The moving image imaging may be performed for further obtaining first to third comparative moving images on a date different from the date of the moving image imaging for obtaining the above first to third comparative moving images.

(2-5. Others)

In the imaging controlling processing according to the present embodiment, in generating the radiographic moving image to be associated with a numerical value which is relatively small among the first to third numerical values as the number of breaths, the first controller 21 may set the number of frames generated per unit time for the radiographic moving image (frame rate) to be smaller than the number of frames per unit time in generating the radiographic moving image to be associated with a numerical value which is relatively large among the first to third numerical values as the number of breaths.

Thereby, it is possible to reduce the exposure level of the subject since slow breathing observation can be performed relatively accurately even for a moving image (rough moving image) that has a small number of frames to be displayed per unit time.

In the above moving image management processing, after executing the above obtaining process, the first controller 21 may store the obtained first to third radiographic moving images in the first storage 22.

In the above moving image management processing, after executing the above obtaining process, the first controller 21 may cause the first display 24 to display the obtained first to third radiographic moving images. Thereby, the user can determine whether or not the radiographic moving image which was generated immediately after the imaging is appropriate for the diagnosis (whether or not the imaging is OK).

In the above moving image management processing, before executing the associating process, the first controller 21 may determine whether or not the obtained first to third radiographic moving images and the first to third comparative moving images can be used for diagnosis (for example, whether or not the user performed the operation indicating imaging is OK to the first operation unit 23) so that the associating process is executed when the first controller 21 determines that the moving images can be used.

[3. Specific Operation of Diagnostic Console]

Next, the specific operation of the diagnostic console 3 included in the above system 100 will be described.

Figure 4:
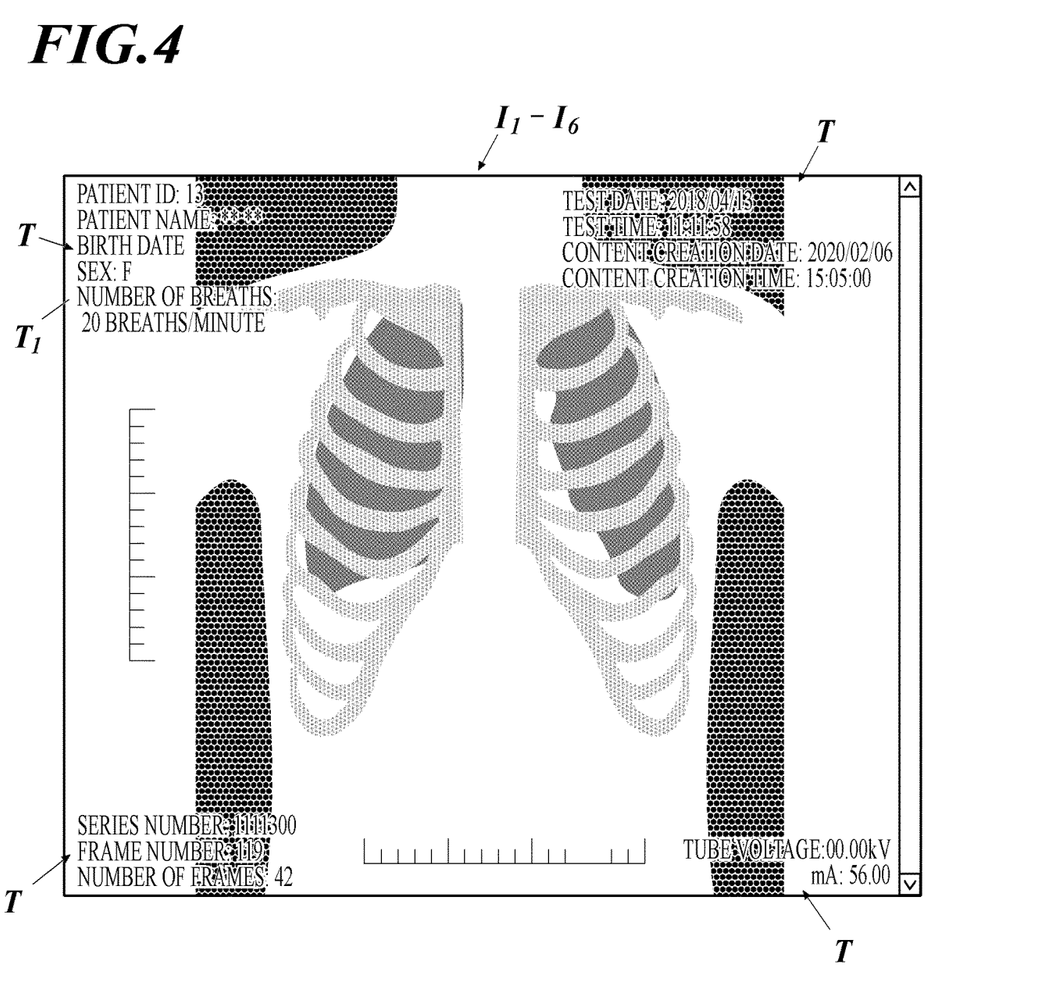
FIG. 4 is a view showing an example of a radiographic moving image displayed by a diagnostic console in FIG. 1.
Figure 5:
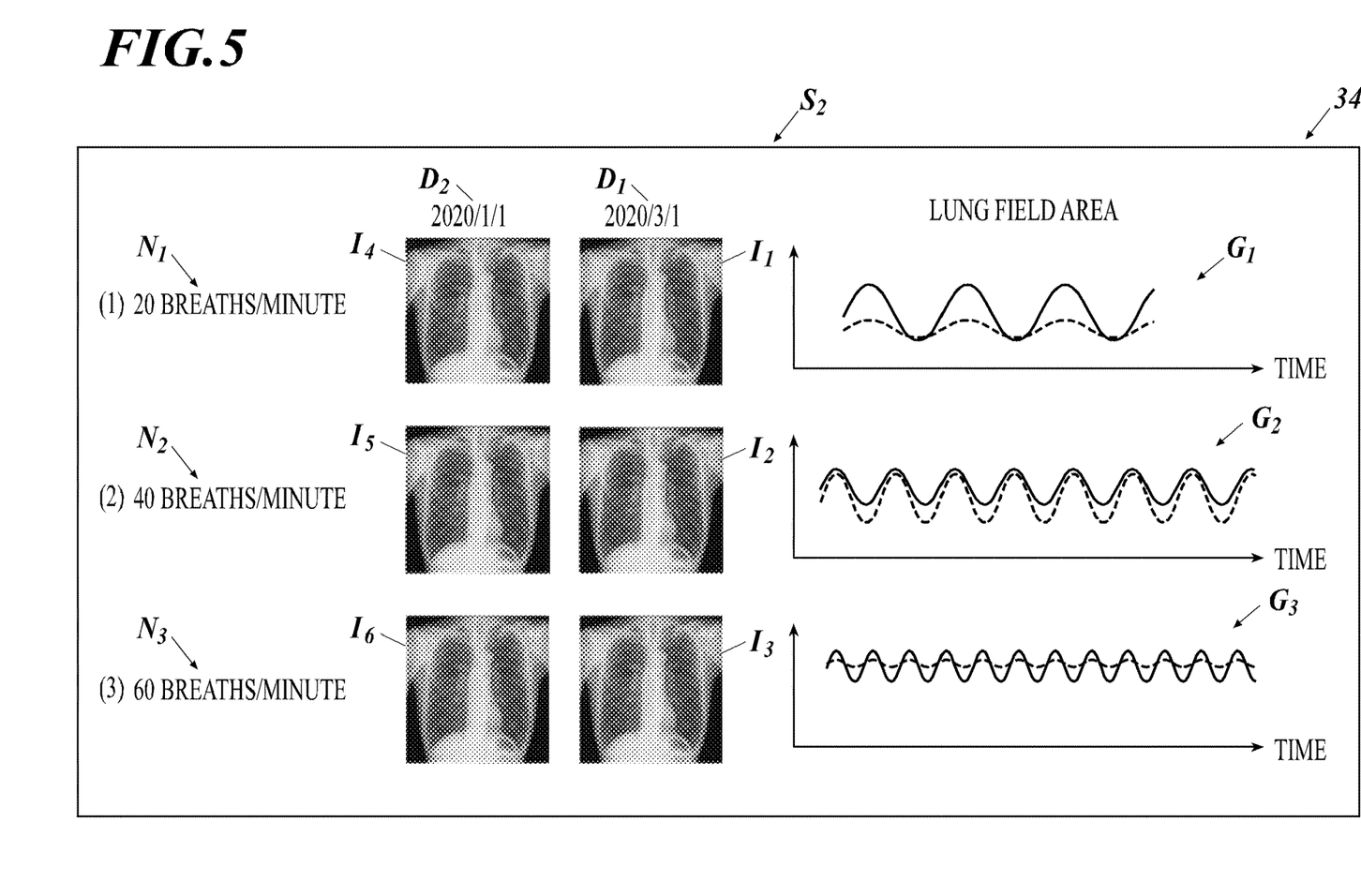
FIG. 5 is a view showing an example of diagnostic screen displayed by the diagnostic console in FIG. 1.

FIG. 4 is a view showing an example of the radiographic moving image displayed by the diagnostic console. FIG. 5 is a view showing an example of a diagnostic screen $S_2$ displayed by the diagnostic console 3.

(3-1. Analysis Operation)

The second controller 31 executes analysis processing in response to satisfaction of a predetermined condition (for example, obtaining of the radiographic moving image from the imaging console 2, execution of a predetermined operation to the second operation unit 33, etc.) as a trigger.

In this analysis processing, the second controller 31 analyzes the first radiographic moving image which was generated by the moving image generator and calculates an index regarding a site which moves in accordance with breathing.

The index includes at least one of the lung field area, density of lung field, length of lung field (distance between lung apex and diaphragm), position of diaphragm, thorax width and the like.

The index also includes a change rate (speed, acceleration) of each of the above values.

In a case where the analysis target site is a site that repeats a cyclic movement, the index also includes the cycle of the movement, the number of repeats of the movement per unit time, and the like.

Various types of known techniques can be used for calculation of the index.

For example, in a case where the first radiographic moving image is analyzed and the number of breaths per unit time is calculated as the index, the first number of times is obtained from the first radiographic moving image.

The second controller 31 forms an analyzing unit by executing such analysis processing.

In a case where the second numerical value and the third numerical value are input to the setting screen $S_1$ of the imaging console 2, the second controller 31 according to the present embodiment repeats the operation similar to that of the analysis operation which has been described above for the second and third radiographic moving images.

In a case where the first to third comparative moving images were generated on a date different from the date on which the first to third radiographic moving images were generated, the second controller 31 repeats the operation similar to the analysis operation which has been described above for the first to third comparative moving images.

(3-2. Display Operation)

The second controller 31 executes display processing in response to satisfaction of a predetermined condition (for example, receiving of at least one of the first to third radiographic moving images and the first to third comparative moving images, execution of a predetermined operation to the second operation unit 33, etc.) as a trigger.

In this display processing, as shown in FIG. 4, the second controller 31 causes the second display 34 to display at least one of the first to third radiographic moving images $I_1$ to $I_3$ and the first to third comparative moving images $I_4$ to $I_6$, for example.

When the second controller 31 causes the second display 34 to display the radiographic moving images $I_1$ to $I_6$, the second controller 31 can cause the second display 34 to display part of tag information T including the information $T_1$ on the number of breaths in a region overlapping, as little as possible, with the region showing the diagnosis target site of the subject M (for example, four corners of the radiographic moving images $I_1$ to $I_6$).

In the display processing according to the present embodiment, the second controller 31 can also cause the second display 34 to display at least two of the first to third radiographic moving images $I_1$ to $I_3$ and the first to third comparative moving images $I_4$ to $I_6$.

In the display processing according to the present embodiment, the second controller 31 causes the second display 34 to display a diagnostic screen $S_2$ as shown in FIG. 5, for example.

The second controller 31 causes the second display 34 to display the first to third radiographic moving images $I_1$ to $I_3$ and the first to third comparative moving images $I_4$ to $I_6$, on this diagnostic screen $S_2$.

In the display processing according to the present embodiment, on the basis of the associated numbers of breaths, the second controller 31 finds out the first to third radiographic moving images $I_1$ to $I_3$ and the first to third comparative moving images $I_4$ to $I_6$, and causes the second display 34 to display them.

To be specific, the second controller 31 finds out radiographic moving images of a same imaging date, and causes the second display 34 to display the moving images to be arranged in a vertical (horizontal) direction in increasing (decreasing) order of the associated number of breaths. The second controller 31 finds out radiographic moving images of a same number of breaths which is associated, and causes the second display 34 to display the moving images to be arranged in a horizontal (vertical) direction in advancing (backward) order of the imaging date.

In the display processing according to the present embodiment, the second controller 31 causes the second display 34 to display the index which was calculated in the above analysis processing.

In the display processing according to the present embodiment, the second controller 31 causes the second display 34 to display the index in the form of graphs $G_1$ to $G_3$ having the elapsed time (frame number) as the horizontal axis and the index value as the vertical axis.

The index may be displayed by a numerical value, or may be superimposed on the radiographic moving image as an annotation.

In a case where multiple types of indexes has been calculated, the second controller 31 may cause the second display 34 to display the multiple indexes at the same time, or may cause the second display 34 to switch the displayed index according to operations performed to the second operation unit 33.

In the display processing according to the present embodiment, the second controller 31 causes the second display 34 to display the numbers of breaths $N_1$ to $N_3$ (at least one of the first to third numerical values), which are associated with the displayed radiographic moving images $I_1$ to $I_6$, so as to be lateral to the corresponding radiographic moving images $I_1$ to $I_6$.

In the display processing according to the present embodiment, the second controller 31 causes the second display 34 to display the imaging date $D_1$ of the radiographic moving images $I_1$ to $I_3$ and the imaging date $D_2$ of the comparative moving images $I_4$ to $I_6$ above the corresponding radiographic moving images $I_1$ to $I_6$.

By using such a diagnostic screen $S_2$, it is possible to easily perform diagnosis diagnosing what number of breaths or more per unit time causes the dynamic pulmonary hyperinflation to occur, and diagnosis diagnosing that the symptom is getting better or worse compared to the symptom at the time of previous imaging.

[4. Effect]

As described above, a moving image management apparatus according to the present embodiment and a system 100 including the moving image management apparatus respectively associate numbers of breaths at the time of imaging with the first to third radiographic moving images which were generated by performing moving image imaging of the chest of a subject on one day, and respectively associate numbers of breaths at the time of imaging with the first to third comparative moving images which were generated by performing moving image imaging of the chest of the subject on another day.

Thus, according to the moving image management apparatus and the system 100, the user can easily find out the radiographic moving images of a same imaging date and different numbers of breaths per unit time and radiographic moving images of a same number of breaths and different obtaining dates from among the multiple radiographic moving images.

[5. Others]

The present invention is not limited to the above embodiment or the like, and modification can be made as needed within the scope of the present invention.

For example, though the system 100 according to the above embodiment includes the separate imaging console 2 and diagnostic console 3, the imaging console 2 and the diagnostic console 3 may be integrated.

In the system 100 according to the above embodiment, transmission and reception of image data and the like are performed via the communication network N. However, the image data and the like may be transmitted and received via a storage medium.

The above description discloses an example of using a hard disk, semiconductor nonvolatile memory, or the like as a computer readable medium of a program according to the present invention. However, the medium is not limited to this example. As other computer readable medium, a portable recording medium such as a CD-ROM can be applied.

A carrier wave can also be applied as a medium providing the program data according to the present invention via a communication line.

Although embodiments of the present invention have been described and illustrated in detail, the disclosed embodiments are made for purposes of illustration and example only and not limitation. The scope of the present invention should be interpreted by terms of the appended claims.

What is claimed is:

1. A non-transitory recording medium storing a computer readable program that causes a computer of a moving image management apparatus, which manages a radiographic moving image, to perform:

obtaining that is obtaining a first radiographic moving image and a second radiographic moving image, the first radiographic moving image showing a movement of a subject while breathing is repeated a first number of times per unit time, and the second radiographic moving image showing a movement of the subject while breathing is repeated a second number of times that is different from the first number of times per the unit time; and associating that is associating respective numbers of breaths during imagings with the first radiographic moving image and the second radiographic moving image that are obtained in the obtaining, wherein the program further causes the computer to perform receiving that is receiving each of input of a first numerical value and input of a second numerical value, and the associating includes associating, with the first radiographic moving image, the first numerical value as a number of breaths among the numbers of breaths and associating, with the second radiographic moving image, the second numerical value as a number of breaths among the numbers of breaths.

2. The recording medium according to claim 1, wherein the associating includes writing the respective numbers of breaths as image supplementary information into data of the first radiographic moving image and data of the second radiographic moving image.

3. The recording medium according to claim 1, wherein the program further causes the computer to perform imaging controlling that is causing a moving image generator, which generates a radiographic moving image, to generate the radiographic moving image to be associated with the first numerical value as the number of breaths and generate the radiographic moving image to be associated with the second numerical value as the number of breaths.

4. The recording medium according to claim 3, wherein the imaging controlling includes setting a number of frames, which are generated per the unit time for the radiographic moving image in generating of the radiographic moving image to be associated with a smaller numerical value among the first numerical value and the second numerical value as the number of breaths, to be smaller than a number of frames that are generated per the unit time in generating of the radiographic moving image to be associated with a larger numerical value among the first numerical value and the second numerical value as the number of breaths.

5. The recording medium according to claim 1, wherein the obtaining includes obtaining a first comparative moving image and a second comparative moving image, the first comparative moving image showing a movement of the subject while breathing is repeated the first number of times per the unit time on a day different from a day on which the first radiographic moving image is generated, and the second comparative moving image showing a movement of the subject while breathing is repeated the second number of times per the unit time on a day different from a day on which the second radiographic moving image is generated, and the associating includes associating respective numbers of breaths during imagings with the first comparative moving image and the second comparative moving image that are obtained in the obtaining.

6. The recording medium according to claim 3, wherein the program further causes the computer to perform notifying that is causing a notifier to repeatedly notify at least one of an expiration instruction and an inspiration instruction the first number of times per the unit time and causing the notifier to repeatedly notify at least one of the expiration instruction and the inspiration instruction the second number of times per the unit time in parallel with execution of the imaging controlling, the expiration instruction instructing to perform an expiratory movement and the inspiration instruction instructing to perform an inspiratory movement.

7. A moving image management apparatus comprising a hardware processor that obtains a first radiographic moving image and a second radiographic moving image, the first radiographic moving image showing a movement of a subject while breathing is repeated a first number of times per unit time, and the second radiographic moving image showing a movement of the subject while breathing is repeated a second number of times that is different from the first number of times per the unit time, and associates respective numbers of breaths during imagings with the first radiographic moving image and the second radiographic moving image that are obtained, wherein the hardware processor further receives each of input of a first numerical value and input of a second numerical value, the first radiographic moving image is associated with the first numerical value as a number of breaths among the numbers of breaths, and the second radiographic moving image is associated with the second numerical value as a number of breaths among the numbers of breaths.

8. A moving image display system comprising:

a moving image generator that generates a first radiographic moving image and a second radiographic moving image, the first radiographic moving image showing a movement of a subject while breathing is repeated a first number of times per unit time, and the second radiographic moving image showing a movement of the subject while breathing is repeated a second number of times that is different from the first number of times per the unit time; and a hardware processor that associates respective numbers of breaths during imagings with the first radiographic moving image and the second radiographic moving image that are generated by the moving image generator, wherein the hardware processor further receives each of input of a first numerical value and input of a second numerical value, the first radiographic moving image is associated with the first numerical value as a number of breaths among the numbers of breaths, and the second radiographic moving image is associated with the second numerical value as a number of breaths among the numbers of breaths.

9. The moving image display system according to claim 8, wherein the moving image generator generates a first comparative moving image and a second comparative moving image, the first comparative moving image showing a movement of the subject while breathing is repeated the first number of times per the unit time on a day different from a day on which the first radiographic moving image is generated, and the second comparative moving image showing a movement of the subject while breathing is repeated the second number of times per the unit time on a day different from a day on which the second radiographic moving image is generated, and the hardware processor associates respective numbers of breaths during imagings with the first comparative moving image and the second comparative moving image that are generated by the moving image generator.

10. The moving image display system according to claim 9, wherein the hardware processor analyzes each of the first radiographic moving image and the second radiographic moving image generated by the moving image generator, and calculates an index regarding a site that moves in accordance with breathing.

11. The moving image display system according to claim 10, further comprising a display that displays the first radiographic moving image, the second radiographic moving image, the first comparative moving image and the second comparative moving image.

12. The moving image display system according to claim 11, wherein the display further displays the index that is calculated by the hardware processor.

* * * * *